US011339187B2

(12) United States Patent
Breitler

(10) Patent No.: US 11,339,187 B2
(45) Date of Patent: May 24, 2022

(54) PROCESS FOR THE PREPARATION OF GALNAC OLIGONUCLEOTIDE CONJUGATES

(71) Applicant: Hoffmann-La Roche Inc., Little Falls, NJ (US)

(72) Inventor: Simon Breitler, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/939,849

(22) Filed: Jul. 27, 2020

(65) Prior Publication Data

US 2020/0361983 A1 Nov. 19, 2020

Related U.S. Application Data

(63) Continuation of application No. PCT/EP2019/052014, filed on Jan. 28, 2019.

(30) Foreign Application Priority Data

Jan. 29, 2018 (EP) .................................... 18153875

(51) Int. Cl.
| | | |
|---|---|---|
| C07H 21/00 | (2006.01) | |
| C07H 5/06 | (2006.01) | |
| C07H 15/08 | (2006.01) | |
| C07D 207/46 | (2006.01) | |
| C07H 1/00 | (2006.01) | |

(52) U.S. Cl.
CPC ........... *C07H 21/00* (2013.01); *C07D 207/46* (2013.01); *C07H 1/00* (2013.01); *C07H 5/06* (2013.01); *C07H 15/08* (2013.01)

(58) Field of Classification Search
None
See application file for complete search history.

(56) References Cited

U.S. PATENT DOCUMENTS

| 10,780,054 B2 * | 9/2020 | Ketterer .................. A61P 31/00 |
| 2011/0207799 A1 * | 8/2011 | Rozema ................... A61P 31/12 |
| | | 514/44 A |

FOREIGN PATENT DOCUMENTS

| WO | 2017/021385 A1 | 2/2017 |
| WO | 2018/215391 A1 | 11/2018 |

OTHER PUBLICATIONS

Lajimi et al., "Sample self-displacement purification of an antisense oligonucleotide by anion exchange membrane chromatography" Abstracts of Papers, 225th ACS National Meeting, New Orleans, LA, United States, Mar. 23-27, 2003 BIOT-274 (Year: 2003).*
Bannwarth et al., "Formation of Carboxamides with N,N,N',N'-Tetramethyl (Succinimido) Uronium Tetrafluoroborate in Aqueous / Organic Solvent Systems" Tetrahedron Letters 32(9):1157-1160 ( 1991).
Han et al., "Recent development of peptide coupling reagents in organic synthesis" Tetrahedron 60(11):2447-2467 ( 2004).
International Preliminary Report on Patentability for PCT/EP2019/052014 dated Aug. 4, 2020.
International Search Report for PCT/EP2019/052014 dated Apr. 17, 2019.

* cited by examiner

*Primary Examiner* — Eric Olson
(74) *Attorney, Agent, or Firm* — Genentech, Inc.; Kevin M. Clark

(57) ABSTRACT

The invention comprises a process for the preparation of GalNAc oligonucleotide conjugates which comprises the coupling of a GalNAc cluster compound of the formula

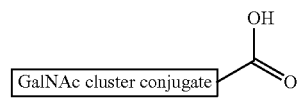

or corresponding salts, enantiomers and/or a stereoisomer thereof, with an oligonucleotide in the presence of an O-dicarboximidouronium salt as coupling agent.

16 Claims, No Drawings
Specification includes a Sequence Listing.

PROCESS FOR THE PREPARATION OF GALNAC OLIGONUCLEOTIDE CONJUGATES

CROSS REFERENCE TO RELATED APPLICATIONS

This application is a continuation of International Application No. PCT/EP2019/052014 having an international filing date of Jan. 28, 2019, the entire contents of which are incorporated herein by reference, and which claims benefit under 35 U.S.C. § 119 to European Patent Application No. 18153875.2 filed on Jan. 29, 2018.

FIELD OF THE INVENTION

The invention relates to a process for the preparation of GalNAc oligonucleotide conjugates which comprises the coupling of a GalNAc cluster compound of the formula

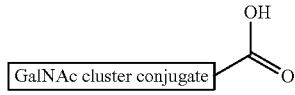

I or of corresponding salts, enantiomers and/or a stereoisomer thereof, with an oligonucleotide in the presence of an O-dicarboximidouronium salt as coupling agent.

The coupling procedure in principle follows the methods well known and extensively described for the formation of a peptide linkage between an amine and a carboxylic acid and as a rule comprises an activation of the carboxylic acid and the subsequent couplings with the amine.

Coupling reactions of a GalNAc cluster and an oligonucleotide are also well described in the art. More recent illustrative publications are the US Patent Application Publication US 2011/0207799, the PCT Publication WO2017/021385 which refers in example 11 to the published US Patent Application or PCT Publication WO2018/215391

SEQUENCE LISTING

The instant application contains a Sequence Listing submitted via EFS-Web and hereby incorporated by reference in its entirety. Said ASCII copy, created on Jul. 27, 2020, is named P34628US_SeqList.txt, and is 896 bytes in size.

BACKGROUND

The state-of-the-art methods are as a rule using diimide coupling reagents such as DCC, DIC or EDC or phosphonium salts such as PyBOP, require the additional use of organic bases and typically run in polar, aprotic solvents such as in DMF or DMSO. The coupling of oligonucleotides prefers aqueous conditions; the state of the art conditions are therefore not favorable to apply.

Also, the use of these reagents require protonation of the metal salts of GalNAc prior to activation. The most beneficial acid for this purpose was found to be $H_3PO_4$. However, it was observed that the use of $H_3PO_4$ leads to phosphorylation of GalNAc sugar units in the conjugated product. These phosphorylated side products cannot be separated by usual purification methods.

The state of the art processes meets the requirements for a lab scale synthesis. With GalNAc oligonucleotides becoming promising drug candidates entering clinical phases more efficient, more economic and commercially applicable larger scale manufacturing processes are required.

In particular processes are desired which do not require prior protonation of metal salts of GalNAc by $H_3PO_4$ in order to avoid phosphorylated side products.

Furthermore, the excess of GalNAc cluster which is usually employed in a 3-fold or higher excess to ensure complete conjugation of the limiting oligonucleotide needs to be minimized.

BRIEF SUMMARY

The object of the present invention therefore was to substantially improve the processes known in the art, particularly to optimize reaction conditions and parameters for both the activation and the coupling step and to minimize side product formation.

It was found that the object of the invention could be reached with the novel process for the preparation of GalNAc oligonucleotide conjugates which comprises the coupling of a GalNAc cluster compound of the formula

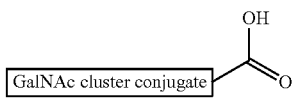

I or of corresponding salts, enantiomers and/or a stereoisomer thereof, with an oligonucleotide in the presence of an O-dicarboximidouronium salt as coupling agent.

DETAILED DESCRIPTION

The following definitions are set forth to illustrate and define the meaning and scope of the various terms used to describe the invention herein.

Whenever a chiral carbon is present in a chemical structure, it is intended that all stereoisomers associated with that chiral carbon are encompassed by the structure as pure stereoisomers as well as mixtures thereof.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "$C_{2-12}$-alkyl" likewise denotes a monovalent linear or branched saturated hydrocarbon group of 2 to 12 carbon atoms, and in more particular embodiments 4 to 8 carbon atoms. Examples of alkyl include ethyl, propyl, isopropyl, n-butyl, iso-butyl, sec-butyl, or tert-butyl and pentyl, hexyl, heptyl, octyl, nonyl, decyl, undecyl and dodecyl and its isomers.

The term "hydroxy-protecting group" and the term "ester protecting group" denote groups which intended to protect a hydroxy group and include ester- and ether-forming groups, in particular tetrahydropyranyl, acyl groups, carbamoyl, benzyl and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. Preferred are the acyl groups, particularly a $C_{1-12}$-alkylcarbonyl group, more particularly a $C_{1-6}$-alkylcarbonyl group which is optionally substituted by $C_{1-6}$-alkyl or phenyl. More preferred hydroxy protecting groups can be selected from acetyl, pivaloyl or benzoyl, whereby acetyl is the most preferred hydroxy protecting group.

The term "alkali" encompasses the alkali metals lithium, sodium and potassium, particularly sodium and potassium with preference to sodium.

The term "earth alkali" encompasses the earth alkali metals calcium and magnesium, but particularly calcium.

The term GalNAc cluster conjugate stands for an asialoglycoprotein receptor targeting moiety which may be used to target the oligonucleotide compound to hepatotcytes and accordingly to treat liver diseases. Typically, the moiety comprises galactosamine, preferably N-acetylgalactosamine.

In a preferred embodiment the term GalNAc cluster conjugate comprises three galactosamine moieties, more preferably three N-acetylgalactosamine moieties, which are linked to a central branch point via a suitable linker.

Suitable linkers which may vary in length, hydrophilic-hydrophobic balance and spatial geometry are described for instance in Huang et al., Bioconjugate Chem. 2017, 28, 283-295.

Preferred linkers are alkylene linkers, ethylene glycol linkers or alkylene linkers which contain one or more, preferably one peptide functionality (—CO—NH—) in the alkylene chain.

In the case of multiple linkers, such as in the preferred embodiment where three N-acetylgalactosamine moieties are linked to a central branch point, the individual linkers may vary, but preferably are the same.

Preferred linker is the ethylene glycol linker.

The term alkylene linker in this context means a "$C_{2-12}$-alkylene bridge", particularly a bivalent linear or branched saturated hydrocarbon group of 2 to 12 carbon atoms, in a more particular embodiment 4 to 8 carbon atoms and in an even more particular embodiment of 6 carbon atoms. Particular examples are butylene, pentylene, hexylene, heptylene or octylene and its isomers, but preferably n-hexylene.

The term "ethylene glycol linker" stands for —$(CH_2)_2$—O— units which as a bridging units can contain 1 to 10 ethylene glycol units, preferably 2 to 6 ethylene glycol, more preferably 3 ethylene glycol units.

The term "branch point" in this context typically means a small molecule which permits attachment of the three galactose derivatives and further permits attachment of the branch point to the oligomer. Preferable branch point molecule is di-lysine. Di-lysine contains three amine groups through which three galactosamine-linker-derivatives may be attached and a carboxyl group through which the GalNAc cluster may be attached to the oligonucleotide.

In a preferred embodiment the GalNac cluster conjugate has the formula Ib

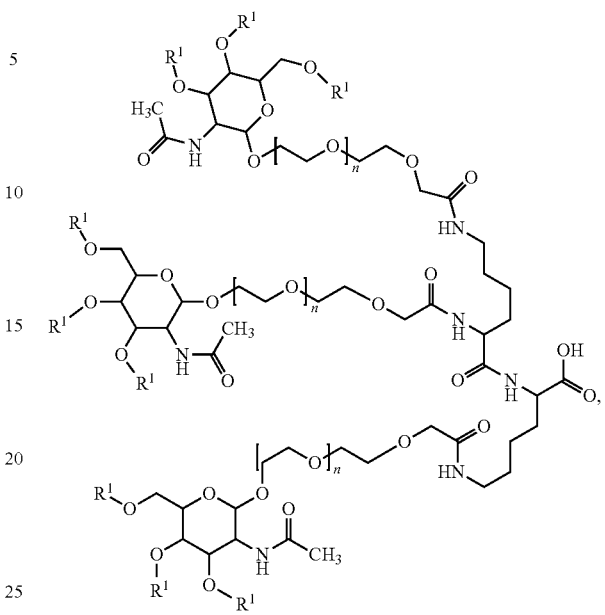

Ib wherein $R^1$ is hydrogen or a hydroxy protecting group, preferably hydrogen or acetyl, more preferably hydrogen and n is an integer from 0 to 10, preferably 1 to 5, more preferably 2, corresponding salts, enantiomers and/or a stereoisomer thereof.

In a further preferred embodiment the GalNac cluster conjugate has the formula Ic

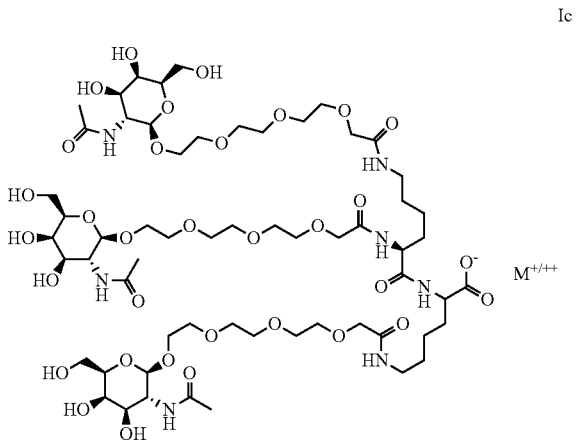 [SMILES: CC(=O)N[C@H]1[C@H](OCCOCCOCCOCC(=O)NCCCCC(NC(=O)[C@H](CCCCNC(=O)COCCOCCOCCO[C@@H]2O[C@H](CO)[C@H](O)[C@H](O)[C@H]2NC(C)=O)NC(=O)COCCOCCOCCO[C@@H]2O[C@H](CO)[C@H](O)[C@H](O)[C@H]2NC(C)=O)C(=O)[O-])O[C@H](CO)[C@H](O)[C@@H]1O]

Ic wherein $M^{+/++}$ is the cation of an alkali metal or of an earth alkali metal as defined above, preferably of an alkali metal and more preferably sodium.

The GalNAc cluster conjugate can for instance be prepared following the methods described in the PCT Publication WO2017/021385 and as shown in the scheme below.

Scheme 1

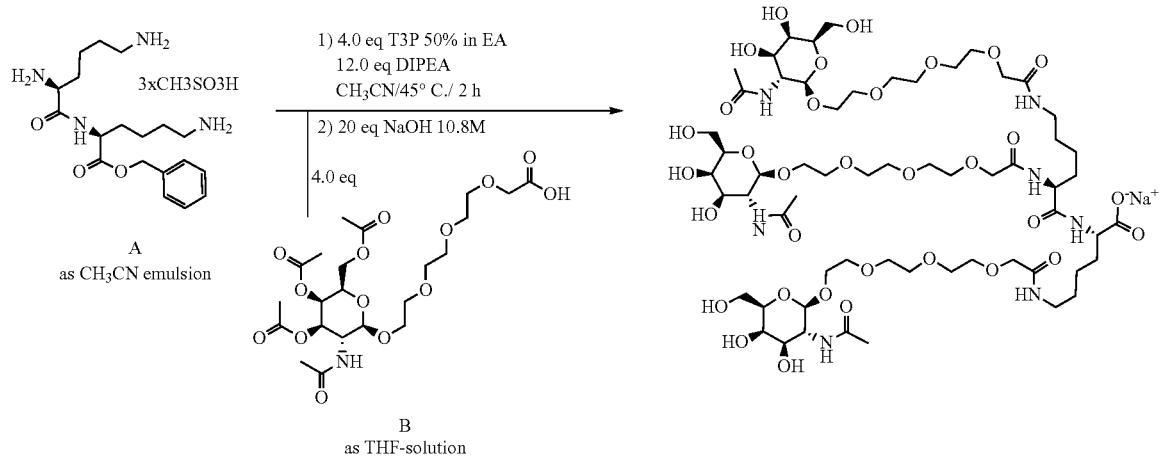

The term 5'amino modified is used in connection with the term 5' amino-modified oligonucleotide and determines a reactive amino group covalently bound to a linker which, as amino linker, is attached at the 5' terminal group of an oligonucleotide. The linker preferably is an aliphatic alkyl group of 2 to 12 carbon atoms or an ethylene glycol linker containing 1 to 10 ethylene glycol units.

The preferred 5'amino-modifier accordingly is selected from an optionally amino group protected amino $C_{2-12}$-alkyl linker, preferably an optionally amino group protected amino $C_{4-8}$-alkyl linker more preferably a $C_6$-alkyl linker.

Suitable amino protecting groups for the 5'amino modified oligonucleotide are trifluoroacetyl (TFA) or monomethoxytrityl (MMT).

As a rule, the amino linker is introduced via a commercially available amino linker phosphoroamidite such as for instance via the TFA- or MMT-$C_6$-linker phosphoroamidites e.g. from Sigma Aldrich or via the 5' amino modifier TEG (triethyleneglycol) CE phosphoroamidite from Glen Research.

The term oligonucleotide as used herein is defined as it is generally understood by the skilled person as a molecule comprising two or more covalently linked nucleotides. For use as a therapeutically valuable oligonucleotide, oligonucleotides are typically synthesized as 7 to 30 nucleotides, preferably 10 to 25 nucleotides in length.

The oligonucleotides may consist of optionally modified DNA, RNA or LNA nucleoside monomers or combinations thereof.

The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, RNA or LNA nucleoside by the introduction of one or more modifications of the sugar moiety or the nucleo base moiety. In a preferred embodiment the modified nucleoside comprises a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleosides are as a rule linked by a phosphodiester (P=O) and/or a phosphorothioate (P=S) internucleoside linkage which covalently couples two nucleosides together.

Accordingly, in some oligonucleotides all internucleoside linkages may consist of a phosphodiester (P=O), in other oligonucleotides all internucleoside linkages may consist of a phosphorothioate (P=S) or in still other oligonucleotides the sequence of internucleoside linkages vary and comprise both phosphodiester (P=O) and phosphorothioate (P=S) internucleoside.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}C$ (5-methyl cytosine) for LNA nucleoside and with small letters a,t,g,c and $^{Me}C$ for DNA nucleosides. Modified nucleobases include but are not limited to nucleobases carrying protecting groups such as tert.butylphenoxyacetyl, phenoxyacetyl, benzoyl, acetyl, isobutyryl or dimethylformamidino (see Wikipedia, Phosphoramidit-Synthese, https://de.wikipedia.org/wiki/Phosphoramidit-Synthese of Mar. 24, 2016).

Preferably the oligonucleotide consists of optionally modified DNA, RNA or LNA nucleoside monomers or combinations thereof and is 10 to 25 nucleotides in length.

The principles of the oligonucleotide synthesis are well known in the art and well described in literature and public for a like Wikipedia (see e.g. Oligonucleotide synthesis; Wikipedia, the free encyclopedia; https://en.wikipedia.org/wiki/Oligonucleotide_synthesis, of Mar. 15, 2016).

Larger scale oligonucleotide synthesis nowadays is carried automatically using computer controlled synthesizers.

As a rule, oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase®HL support from Kinovate.

The oligonucleotide synthesis in principle is a stepwise addition of nucleotide residues to the 5'-terminus of the growing chain until the desired sequence is assembled.

As a rule, each addition is referred to as a synthetic cycle and in principle consists of the chemical reactions $a_1$) de-blocking the protected hydroxyl group on the solid support, $a_2$) coupling the first nucleoside as activated phosphoramidite with the free hydroxyl group on the solid support, $a_3$) oxidizing or sulfurizing the respective P-linked nucleoside to form the respective phosphotriester (P=O) or the respective phosphorothioate (P=S);

$a_4$) optionally, capping any unreacted hydroxyl groups on the solid support;

$a_5$) de-blocking the 5' hydroxyl group of the first nucleoside attached to the solid support;

$a_6$) coupling the second nucleoside as activated phosphoramidite to form the respective P-linked dimer;

$a_7$) oxidizing or sulfurizing the respective P-linked dinucleoside to form the respective phosphotriester (P=O) or the respective phosphorothioate (P=S);

$a_8$) optionally, capping any unreacted 5' hydroxyl groups;

$a_9$) repeating the previous steps $a_5$ to $a_8$ until the desired sequence is assembled.

As outlined above the process of the present invention is characterized by the coupling of a GalNAc cluster compound of the formula

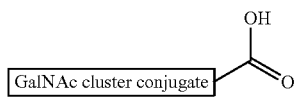

I or of corresponding salts, enantiomers and/or a stereoisomer thereof, with an oligonucleotide in the presence of an O-dicarboximidouronium salt as coupling agent.

O-dicarboximidouronium salts are as a rule commercially available or can be synthesized according to processes known in literature for instance Knorr et al, Tetrahedron Letters, Vol. 30, No. 15, 1927-1930 (1989).

Preferably the O-dicarboximidouronium salts are O-dicarboximidouronium hexafluorphosphates or O-dicarboximidouronium tetrafluoroborates.

They can be selected from N, N, N', N'-Tetramethyl-O-(bicyclo [2.2.1] hept-5-en-2,3-dicarboximido) uroniumtetrafluoroborat (TNTU) or N, N, N, N-Tetramethyl-O-(N-succinimidyl) uroniumtetrafluorborat (TSTU,), more preferably from N, N, N', N'-Tetramethyl-O-(bicyclo [2.2.1] hept-5-en-2,3-dicarboximido) uroniumtetrafluoroborat (TNTU).

Alternatively, aryltriazoluronium salts such as 2-(1H-Benzotriazol-1-yl)-1,1,3,3-tetramethyluronium-hexafluorophosphate (HBTU) or [O-(7-Azabenzotriazol-1-yl)-N, N, N', N'-tetramethyluronium-hexafluorphosphate] (HATU can be applied. However, they are less preferred.

The process is characterized by an initial activation step a) and a subsequent coupling step b).

Activation Step:

In the activation step the GalNAc conjugate reacts with the coupling agent to form an activated GalNAc conjugate. This activated intermediate can be isolated but as a rule it is further processed in situ in the coupling step.

The GalNac conjugate is, as outlined above, preferably applied in the form of an earth alkali metal- or alkali metal salt, more preferably as sodium salt.

It is also possible to start from GalNac in the carboxylic acid form. In that case previous deprotonation with a suitable base, such as with a tertiary amine like diisopropylethylamine base has to be considered.

Usually 1.0 to 1.5 equivalents, preferably 1.0 to 1.3, more preferably 1.0 to 1.1 equivalents of the GalNac conjugate are suspended in a polar aprotic solvent, suitably in N,N-dimethlylforamide, dimethylsulfoxide or N-methylpyrrolidine, preferably in N,N-dimethylformamide.

1.0 to 1.5 equivalents, preferably 1.0 to 1.3 equivalents more preferably 1.0 to 1.1 equivalents of the coupling agent can then be added.

The activation reaction can take place at a reaction temperature from 0° C. to 40° C., but preferably from 20° C. to 25° C. during 0.5 to 3 h, preferably during 0.5 to 1.5 h more preferably 1 h.

Coupling Step:

To the reaction mixture obtained from the activation step an aqueous solution containing 5% G to 40% G, preferably from 10% G to 20% G of the oligonucleotide can be added. Alternatively, the reaction mixture can be dosed to the aqueous solution of the oligonucleotide.

The pH of the reaction mixture is expediently controlled between 7.0 and 10.0, preferably 8.3 and 9.3.

pH control can be achieved by adding an alkali hydroxide or a suitable basic salt or mixtures thereof.

Typically, sodium hydroxide, an alkali hydrogen carbonate like sodium hydrogen carbonate or an alkali hydrogen phosphate like sodium hydrogen phosphate can be used.

The reaction temperature as a rule is in the range from 0° C. to 40° C., preferably from 20° C. to 25° C.

Full conversion can be reached after 1 to 4 h.

Thereafter the resulting GalNAc oligonucleotide conjugate can be separated and further purified.

The purification of the GalNAc-cluster oligonucleotide conjugate obtained from the previous steps essentially comprises the steps precipitation or chromatography, concentration and isolation.

In a preferred embodiment the purification comprises a) a precipitation with an alcoholic solvent or a chromatography selected from an anion exchange chromatography or reversed phase chromatography followed by b) a concentration step selected from a tangential flow filtration and c) an isolation step selected from lyophilization, filtration or spray drying or a precipitation with an alcoholic solvent.

In a further preferred embodiment the purification comprises a) a reversed phase chromatography, optionally in combination with an anion exchange chromatography, followed by b) a tangential flow filtration and c) a lyophilization.

The purification methods mentioned above are common and well known to the skilled in the field of the present invention.

The term precipitation means the formation of a solid out of a solution usually with the help of a suitable solvent. In the context of the present invention suitable solvents are alcohols, preferably lower alcohols such as ethanol or 1-propanol.

The term chromatography comprises the methods anion exchange chromatography or reversed phase chromatography and combinations thereof.

The anion-exchange chromatography is based on the competitive interaction of charged ions of the sample solution with the buffer medium employed. It can be carried out with conventional, commercially available anion-exchange resins, preferably those with trimethylammonium-functionalization. These phase materials can be obtained for example from GE Healthcare, Tosoh Bioscience, Bio-Rad or Merck. Particular good results have been achieved with the anion-exchange resin TSKgel Super Q-5PW (QAE), available from Tosoh Bioscience.

The reversed-phase chromatography can be carried out with traditional, commercially available phase materials such as a modified silica gel sorbents as stationary phase and suitable organic solvents such as acetonitrile and, if applicable, a buffer. Suitable modified silica gel type phase materials can be selected from Kromasil™C18, Kromasil™C8, YMC Triart C18 and YMC Triart C8. Particular good results have been achieved with the Triart Prep C8-S from YMC.

The term concentration comprises the methods tangential flow filtration or evaporation and combinations thereof.

In the tangential flow filtration or cross flow filtration the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate. The principles of tangential flow filtration are also used in nanofiltration, ultrafiltration, diafiltration and microfiltration processes. Suitable membranes are commercially available, for instance from Merck Millipore under the trade name Pellicon™. Suitable membranes have a molecular weight cut-off (MWCO) of ≤3 kDA. The Merck Millipore Pellicon 2 and 3 membranes with an MWCO of 1 kDA or 3 kDA respectively are preferred.

The term isolation comprises the methods lyophilization, precipitation, spray drying and evaporation. All these terms are well known to the skilled in the art.

By way of illustration the oligonucleotide can be selected from the group consisting of:
AM-C6-5'-caT*$^{Me}$C*A*a*c*t*t*t*c*a*c*t*t*$^{Me}$C*A*G (Oligo 1)
AM-C6-5'-ca$^{Me}$C*$^{Me}$C*t*a*t*t*t*a*a*c*a*-t*c*A*G*A*$^{Me}$C-3' (Oligo 2)
AM-C6-5'-caG*$^{Me}$C*G*t*a*a*a*g*a*g*a*G*G-3' (Oligo 3)
wherein AM-C6 means a C6 amino linker; * stands for phosphorthioate bridges; A, G, T and $^{Me}$C (5-methyl cytosine) are LNA nucleoside monomers and a, t, c, g are DNA nucleoside monomers.

In a non-limiting embodiment, the GalNAc cluster oligonucleotide conjugate may be selected from the group consisting of:
GN2-AM-C6-5'-caT*$^{Me}$C*A*a*c*t*t*t*c*a*c*t*t*$^{Me}$C*A*G (Compound 1)
GN2-AM-C6-5'-ca$^{Me}$C*$^{Me}$C*t*a*t*t*t*a*a*c*a*-t*c*A*G*A*$^{Me}$C-3' (Compound 2)
GN2-AM-C6-5'-caG*$^{Me}$C*G*t*a*a*a*g*a*g*a*G*G-3' (Compound 3)
wherein AM-C6 means a C6 amino linker; * stands for phosphorthioate bridges; A, G, T and $^{Me}$C (5-methyl cytosine) are LNA nucleoside monomers and a, t, c, g are DNA nucleoside monomers and GN2 is the GalNAc cluster moiety which may occur in the form of the stereoisomers GN2a or GN2b, or mixtures thereof of the formula below, wherein R signifies the AM-C6-oligonucleotide tail.

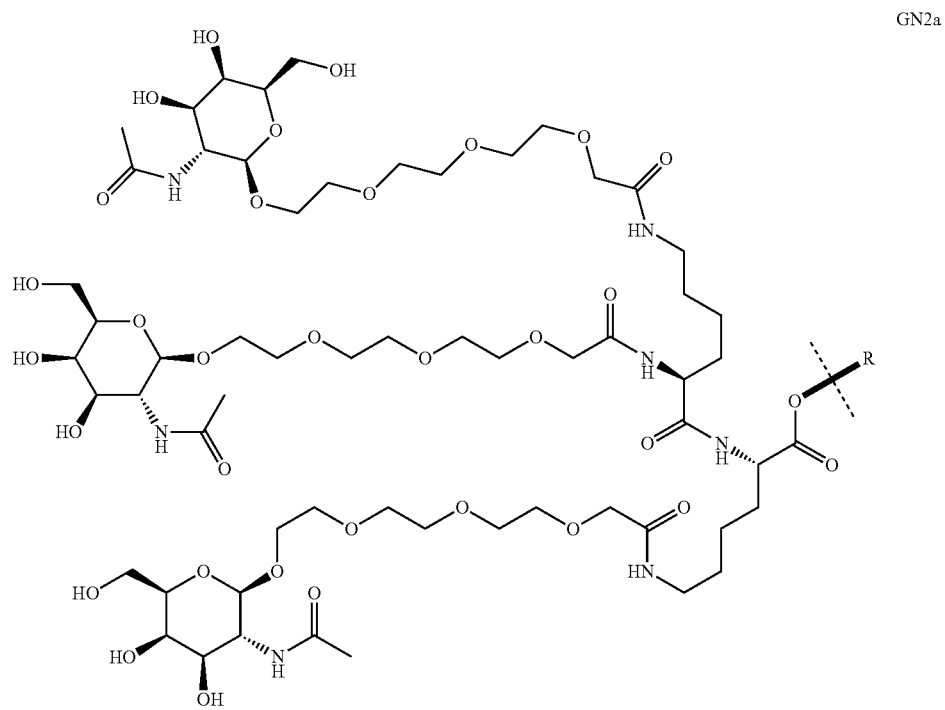

GN2a

GN2b

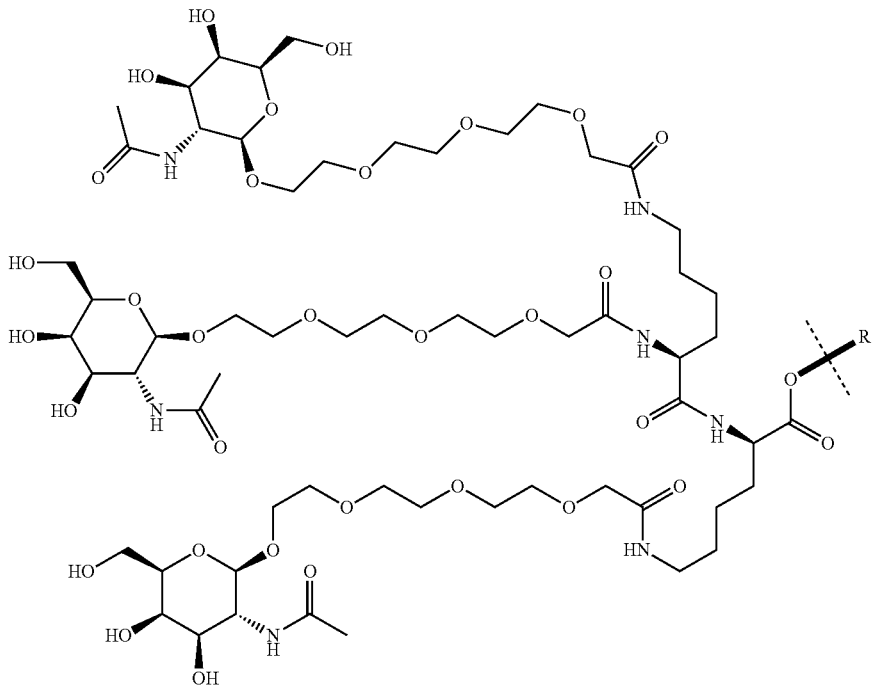

The compounds disclosed herein have the following nucleobase sequences

SEQ ID NO 1:
catcaacttt cacttcag

SEQ ID NO 2:
cacctattta acatcagac

SEQ ID NO 3:
cagcgtaaag agagg

EXAMPLES

Abbreviations:
DMF N,N'-dimethylformamide
DMSO Dimethylsulfoxide
EtOH ethanol
MeCN Acetonitrile
NaCl sodium chloride
NaOAc sodium acetate
NaOH sodium hydroxide
TNTU N,N,N',N'-Tetramethyl-O-(bicyclo[2.2.1]hept-5-en-2,3-dicarboximido) uroniumtetrafluoroborat
TSTU N,N,N',N'-Tetramethyl-O-(N-succinimidyl)uronium tetrafluoroborat
HCTU O-(6-Chlorobenzotriazol-1-yl)-N,N,N,N-tetramethyl uroniumhexafluorophosphate
PyOAP (7-Azabenzotriazol-1-yloxy)tripyrrolidinophosphonium hexafluorophosphate
HBTU 2-(1H-benzotriazol-1-yl)-1,1,3,3-tetramethyluronium hexafluorophosphate
HATU 1-[Bis(dimethylamino)methylene]-1H-1,2,3-triazolo[4,5-b]pyridinium 3-oxid hexafluorophosphate Example 1

GN2-AM-C6-5'-caT*$^{Me}$C*A*a*c*t*t*t*c*a*c*t*t*$^{Me}$C*A*G (Compound 1)

9.8 g (1.53 mmol, theoretical) of the 5'aminomodified oligonucleotide having the sequence AM-C6-5'-caT*$^{Me}$C*A*a*c*t*t*t*c*a*c*t*t*$^{Me}$C*A*G (Oligo 1), desalted by ultrafiltration, was dissolved in aqueous NaHCO$_3$ (0.1 M, 60 ml, pH 8.3) and EtOH (1 ml) was added to avoid foaming.

2.71 g (1.84 mmol, Eq: 1.2) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (12.7 g, 13.5 ml) and TNTU (676 mg, 1.85 mmol, Eq: 1.21) was added. The white suspension was stirred at 20-25° C. for 1 h to afford a clear solution (15.4 g).

The above prepared activated GalNAc solution (12.8 g, 1.0 equiv on 9.8 g theoretical oligo) was added in one pot to the aqueous oligonucleotide solution and stirring was continued for 1.5 h when HPLC showed complete conversion.

The reaction mixture was purified directly by preparative RP-HPLC (YMC Triart C8-S 10 micrometer, MeCN/0.2M NaOAc in H$_2$O, 45° C.). Product-containing fractions were combined and ultrafiltrated and lyophilized to afford the product as a white lyophilized powder (7.5 g, 50%) with a HPLC purity of 80.6% (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.7 (expected 7445.9).

Example 2

GN2-AM-C6-5'-
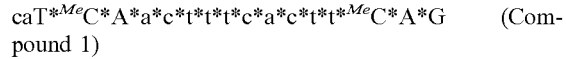 (Compound 1)

13.9 g (1.89 mmol, 87% purity) of the 5'aminomodified oligonucleotide having the sequence AM-C6-5'-caT*$^{Me}$C*A*a*c*t*t*t*c*a*c*t*t*$^{Me}$C*A*G (Oligo 1), being desalted by concentration from NaOH solution, was dissolved in aqueous NaHCO$_3$ (0.1M, 55 ml) and EtOH (2.5 ml) was added. The pH was measured to be 9.8.

3.35 g (2.27 mmol, Eq: 1.2) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxy-ethoxy]ethoxy]ethoxy]acetyl]amino]-2-[[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (15.6 g, 16.5 ml) and TNTU (834 mg, 2.28 mmol, Eq: 1.21) was added. The white suspension was stirred at 20-25° C. for 1 h to afford a clear solution.

The above prepared activated GalNAc solution was added in one pot to the aqueous oligonucleotide solution and stirring was continued for 1 h when HPLC showed complete conversion.

The reaction mixture was triturated with 1-propanol (50 ml) and the suspension stirred at 20-25° C. for 30 min, then let stand for 30 min. The liquid was decanted to leave an oil to which was added 1-propanol (100 ml) and stirring was continued for 16 h. The suspension was filtered, the yellow solid washed twice with 1-propanol (25 ml) and dried in vacuo to afford the product as a yellow solid (14.8 g, 99% recovery) with a HPLC purity of 57.1% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.7 (expected 7445.9).

Example 3

GN2-AM-C6-5'-
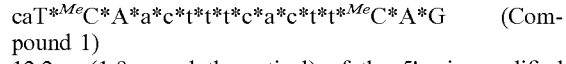 (Compound 1)

12.2 g (1.9 mmol theoretical) of the 5'aminomodified oligonucleotide having the sequence AM-C6-5'-caT*$^{Me}$C*A*a*c*t*t*t*c*a*c*t*t*$^{Me}$C*A*G (Oligo 1), being desalted and purified by IEX-HPLC, was dissolved in aqueous NaHCO$_3$ (0.1M, 55 ml) was added. The pH was measured to be 8.6.

3.37 g (2.28 mmol, Eq: 1.2) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxy-ethoxy]ethoxy]ethoxy]acetyl]amino]-2-[[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (15.6 g, 16.5 ml) and TNTU (839 mg, 2.30 mmol, Eq: 1.21) was added. The white suspension was stirred at 20-25° C. for 1 h to afford a clear solution.

The above prepared activated GalNAc solution was added over 5 min to the aqueous oligonucleotide solution and stirring was continued for 2 h. HPLC showed incomplete conversion and addition activated GalNAc cluster conjugate (prepared from GalNAc sodium salt (561 mg, 0.38 mmol, 0.2 equiv), DMF (2.6 ml) and TNTU (146 mg, 0.4 mmol, 0.21 equiv for 1 h) was added to the reaction mixture. After an additional 30 min, the reaction mixture was triturated with 1-propanol (110 ml) and the suspension stirred at 20-25° C. for 30 min, then let stand for 30 min. The liquid was decanted to leave an oil to which was added 1-propanol (100 ml) and stirring was continued for 16 h. The suspension was filtered, the yellow solid washed twice with 1-propanol (25 ml) and dried in vacuo to afford the product as a yellow solid (14.9 g, 100% recovery) with a HPLC purity of 75.4% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.6 (expected 7445.9).

Example 4

GN2-AM-C6-5'-
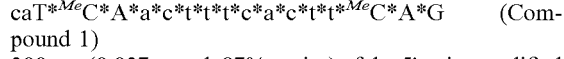 (Compound 1)

200 mg (0.027 mmol, 87% purity) of the 5'aminomodified oligonucleotide having the sequence AM-C6-5'-caT*$^{Me}$C*A*a*c*t*t*t*c*a*c*t*t*$^{Me}$C*A*G (Oligo 1), being desalted by concentration from NaOH solution, was dissolved in aqueous NaHCO$_3$ (0.1M, 0.79 ml) with a pH of 9.0.

40 mg (0.027 mmol, Eq: 1.0) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxy-ethoxy]ethoxy]ethoxy]acetyl]amino]-2-[[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (0.2 ml) and TNTU (10 mg, 0.027 mmol, Eq: 1.0) was added. The white suspension was stirred at 20-25° C. and for 1 h to afford a clear solution.

The above prepared activated GalNAc solution was added in one pot to the aqueous oligonucleotide solution and stirring was continued for 1.5 h.

The reaction mixture was triturated with 1-propanol (4 ml) and the suspension stirred at 20-25° C. for 10 min. The liquid was decanted to leave an oil to which was added 1-propanol (4 ml) and stirring was continued for 17 h. The suspension was filtered, the yellow solid washed twice with 1-propanol (1 ml) and dried in vacuo to afford the product as a yellow solid (150 mg, 70% recovery) with a HPLC purity of 45.8% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.8 (expected 7445.9).

Example 5

GN2-AM-C6-5'-
caT*$^{Me}$C*A*a*c*t*t*t*c*a*c*t*t*$^{Me}$C*A*G (Compound 1)

The procedure from Example 4 was followed using TSTU (9.9 mg, 0.027 mmol, 1.0 equiv) instead of TNTU to afford the product as a yellow solid (160 mg, 75% recovery) with a HPLC purity of 56% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.5 (expected 7445.9).

Example 6

GN2-AM-C6-5'-caG*$^{Me}$C*G*t*a*a*a*g*a*g*a*G*G-3' (Compound 3)

0.5 g (0.08 mmol, 92% purity) of the 5'aminomodified oligonucleotide having the sequence AM-C6-5'-caG*$^{Me}$C*G*t*a*a*a*g*a*g*a*G*G-3' (Oligo 3), being desalted by concentration from NaOH solution, was dissolved in aqueous NaHCO$_3$ (0.1M, 1.98 ml, pH 8.3)

147 mg (99.8 µmol, 1.2 equiv) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (0.8 ml) and TNTU (36.7 mg, 0.10 mmol, Eq: 1.21) was added. The white suspension was stirred at 20-25° C. for 1 h to afford a clear solution.

The above prepared activated GalNAc solution was added over 1 min to the aqueous oligonucleotide solution and stirring was continued for 1 h when HPLC showed complete conversion.

The reaction mixture triturated with 1-propanol (5 ml) and the suspension stirred at 20-25° C. for 30 min, then let stand for 30 min. The liquid was decanted to leave an oil which was added 1-propanol (2.5 ml) and stirring was continued for 16 h. The suspension was filtered, the yellow solid washed twice with 1-propanol (0.9 ml) and dried in vacuo to afford the product as a yellow solid (560 mg, 96%) with a HPLC purity of 60.9% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6639.2 (expected 6637.3).

Example 7

GN2-AM-C6-5'-ca$^{Me}$C*$^{Me}$C*t*a*t*t*t*a*a*c*a*-t*c*A*G*A*$^{Me}$C-3' (Compound 2)

0.5 g (0.07 mmol theoretical) of the 5'aminomodified oligonucleotide having the sequence AM-C6-5'-ca$^{Me}$C*$^{Me}$C*t*a*t*t*t*a*a*c*a*-t*c*A*G*A*$^{Me}$C-3' (Oligo 2), being desalted by concentration from NaOH solution), was dissolved in aqueous NaHCO$_3$ (0.1M, 2.0 ml, pH 8.3)

131 mg (88.5 µmol, 1.2 equiv) of the GalNAc cluster conjugate of the formula 1c with M$^{+/++}$=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (0.65 ml) and TNTU (32.6 mg, 0.09 mmol, Eq: 1.21) was added. The white suspension was stirred at 20-25° C. for 1 h to afford a clear solution.

The above prepared activated GalNAc solution was added over 1 min to the aqueous oligonucleotide solution and stirring was continued for 2.5 h when HPLC showed incomplete conversion and addition activated GalNAc cluster conjugate (prepared from GalNAc sodium salt (32.7 mg, 0.02 mmol, 0.3 equiv), DMF (0.15 ml) and TNTU (8.3 mg, 0.02 mmol, 0.31 equiv for 1 h) was added to the reaction mixture. After an additional 1 h, the reaction mixture triturated with 1-propanol (5 ml) and the suspension stirred at 20-25° C. for 30 min, then let stand for 30 min. The liquid was decanted to leave an oil to which was added 1-propanol (2.5 ml) and stirring was continued for 16 h. The suspension was filtered, the yellow solid washed twice with 1-propanol (0.9 ml) and dried in vacuo to afford the product as a yellow solid (470 mg, 77.6%) with a HPLC purity of 65.6% (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B:

17.5% water/80% CH$_3$OH/0.2M hexafluoro-2-propanol/16.3 mmol triethylamine). UPLC-MS: m/z 7799.6 (expected 7798.2).

Example 8

Large Scale Example

GN2-AM-C6-5'-caT*$^{Me}$C*A*a*c*t*t*t*c*a*c*t*t*$^{Me}$C*A*G  (Compound 1)

1.77 kg of a 20% w/w aqueous solution consisting of the 5' amino modified oligonucleotide having the sequence AM-C6-5'-caT*MeC*A*a*c*t*t*t*c*a*c*t*t*MeC*A*G (Oligo 1) which desalted by ultrafiltration at was adjusted to pH 8.3-8.5 with NaHCO$_3$.

89.8 g (Eq: 1.1) of the GalNAc cluster conjugate of the formula 1c with M+/++=sodium (sodium (2S)-6-[[2-[2-[2-[2-[(2R,3R,4R,5R,6R)-3-acetamido-4,5-dihydroxy-6-(hydroxymethyl) tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) was suspended in DMF (450 ml) and TNTU (22.2 g, Eq: 1.1) was added. The yellowish solution was stirred at 20-25° C. for 1 h.

The above prepared activated GalNAc solution was added over 5 min to the aqueous oligonucleotide solution and stirring was continued for 2 h. When HPLC showed incomplete conversion, additional activated GalNAc solution was prepared as above from GalNAc cluster conjugate of the formula 1c with M+/++=sodium (sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate) (8.2 g), TNTU (2.0 g) in DMF (41 ml). This solution was added to the aqueous oligonucleotide solution in one pot and stirring was continued for an additional hour at 20-25° C.

The reaction mixture was purified directly by preparative RP-HPLC (YMC Triart C8-S 10 micrometer, MeCN/0.2M NaOAc in H2O, 45° C.). Product-containing fractions were combined and ultrafiltrated and lyophilized to afford the product as a white lyophilized powder (210 g, 27%) with a HPLC purity of 91.34% (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7447.7 (expected 7445.9).

When analyzing the purified GN2-AM-C6-5'-caT*MeC*A*a*c*t*t*t*c*a*c*t*t*MeC*A*G by high resolution mass spectrometry, no side products related to GalNAc-sugar phosphorylation were found.

Comparison Example

In Analogy to Example 3A of WO 2018/215391

GN2-AM-C6-5'-caT*MeC*A*a*c*t*t*t*c*a*c*t*t*MeC*A*G  (Compound 1)

GalNAc Activation:

50.3 g (34.1 mmol, 1.6 equiv) GalNAc-cluster-sodium salt was suspended in 250 ml DMF at 20-25° C. and a solution of 1.63 ml (24.1 mmol, 1.13 equiv) aq. phosphoric acid 85% in 250 ml DMF was added. After 5 min at 20-25° C., 5.88 g (51.1 mmol, 2.40 equiv) N-hydroxysuccinimide was added to the colorless solution, followed by addition of 9.80 g (51.1 mmol, 2.40 equiv) EDC.HCl (N-(3-dimethylaminopropyl)-N'-ethylcarbodiimide-hydrochloride) 1. The colorless slightly cloudy solution was stirred for 4 h at 20-25° C. and used in the coupling step.

GalNAc Coupling:

To 2.27 kg of the solution theoretically containing 136.4 g (21.3 mmol, 1.0 equiv) AM-C6-5' caT*MeC*A*a*c*t*t*t*c*a*c*t*t*MeC*A*G-3' as its sodium salt was added 42.8 ml (245 mmol, 11.3 equiv) N-ethyldiisopropylamine and 900 mL DMSO, the solution was warmed to 40-45° C. and added in 1 min to the activated GalNAc solution from above. The yellow solution was stirred for 0.5 h at 40° C. to obtain a crude solution of GalNAcAM-C6-5'caT*MeC*A*a*c*t*t*t*c*a*c*t*t*MeC*A*G-3' as its sodium salt. HPLC showed 53.0% area in crude solution (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/MeCN/0.2M hexafluoro-2-propanol/0.05M hexylamine/0.04M triethylamine, B: CH$_3$OH/MeCN 9:1. This solution was stored at 4° C. until purification. The above coupling procedure was repeated twice on the same scale the three individual reaction mixtures were combined for purification.

The reaction mixture was purified directly by preparative RP-HPLC (YMC Triart C8-S 10 micrometer, MeCN/0.2M NaOAc in H$_2$O, 45° C.). Product-containing fractions were combined and ultrafiltrated and lyophilized to afford the product as a white lyophilized powder (355 g, 30%) with a HPLC purity of 90.35% (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/MeCN M hexafluoro-2-propanol/hexylamine/triethylamine, B: CH$_3$OH/MeCN). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH3OH/0.2M hexafluoro-2-propanol/16.3 mmol trimethylamine, B: 17.5% water/80% CH3OH/0.2M hexafluoro-2-propanol/16.3 mmol triethylamine). UPLC-MS: m/z 7447.7 (expected 7445.9).

The purified GN2-AM-C6-5'-caT*MeC*A*a*c*t*t*t*c*a*c*t*t*MeC*A*G was analyzed by high-resolution mass spectrometry. A side product with mass 7503.27984, attributed to a phosphate diester modified product, wherein one of the three GalNAc sugar units has been modified with a PO$_2^-$ fragment was found in 0.67% abundance. A side product with mass 7521.32758, attributed to a phosphate monoester modified product of structure Y, wherein one the three GalNAc sugar units has been modified with a HPO$_3^-$, was found in 0.79% abundance.

What is claimed is:

1. A process for the preparation of GalNAc oligonucleotide conjugates, the process comprising the coupling of a GalNAc cluster compound of the formula Ib

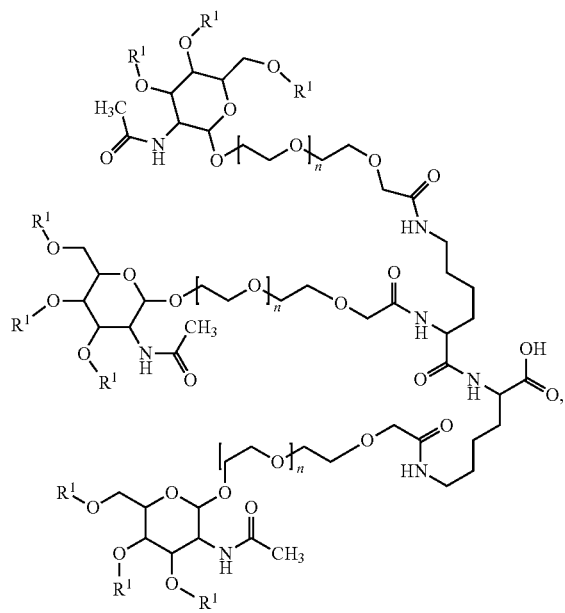

wherein $R^1$ is hydrogen or a hydroxy protecting group and n is an integer from 0 to 10;

with an oligonucleotide in the presence of a O-dicarboximidouronium hexafluorphosphate or a O-dicarboximidouronium tetrafluoroborate coupling agent.

2. The process of claim 1, wherein the GalNac cluster conjugate comprises formula Ic:

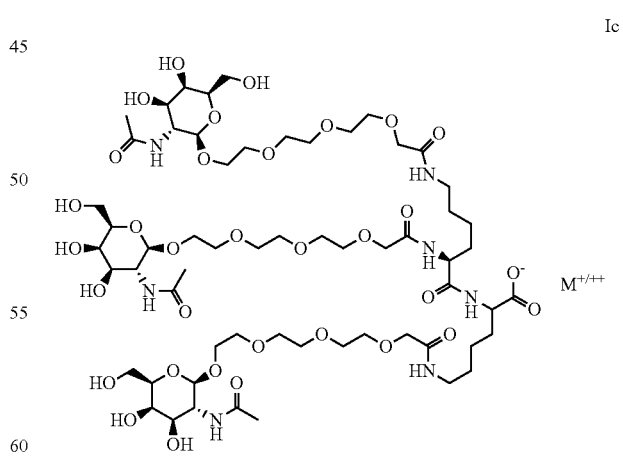

wherein $M^{+/++}$ is a cation of an alkali metal or of an earth alkali metal.

3. The process of claim 1, wherein the O-dicarboximidouronium salt is N, N, N', N'-Tetramethyl-O-(bicyclo[2.2.1]hept-5-en-2,3-dicarboximido)uroniumtetrafluoroborate (TNTU).

4. The process of claim 2, wherein M is sodium or potassium.

5. The process of claim 1, wherein the oligonucleotide is a 5' amino-modified oligonucleotide.

6. The process of claim 5, wherein the 5'amino-modifier is selected from an optionally amino group protected amino $C_{2-12}$-alkyl linker or amino ethylene glycol linker containing 1 to 10 ethylene glycol units.

7. The process of claim 6, wherein an optionally amino group protected amino $C_{2-12}$-alkyl linker is selected.

8. The process of claim 1, wherein the oligonucleotide consists of optionally modified DNA, RNA or LNA nucleoside monomers or combinations thereof and is 7 to 30 nucleotides in length.

9. The process of claim 1, further comprising
a) an activation step, wherein 1.0 to 1.5 equivalents of the GalNAc cluster conjugate of formula I is suspended in a polar aprotic solvent, 1.0 to 1.5 equivalents of the coupling agent is added and the suspension is at a reaction temperature from 0° C. to 40° C.; and
b) a coupling step, wherein the reaction mixture from step a) is mixed with an aqueous solution containing 10% weight to 25% weight of the oligonucleotide at a pH of 8.0 to 10.0 at a reaction temperature from 0° C. to 40° C.

10. The process of claim 9 wherein the polar aprotic solvent is N,N-dimethlylformamide, dimethylsulfoxide or N-methylpyrrolidine.

11. The process of claim 9, further comprising a purification step c).

12. The process of claim 11, wherein the purification step comprises:
a) precipitation with an alcoholic solvent or chromatography selected from an anion exchange chromatography or reversed phase chromatography followed by;
b) a concentration step selected from a tangential flow filtration; and
c) an isolation step selected from lyophilization, filtration or spray drying or a precipitation with an alcoholic solvent.

13. The process of claim 1, wherein the O-dicarboximidouronium tetrafluoroborate is N, N, N', N'-Tetramethyl-O-(bicyclo [2.2.1] hept-5-en-2,3-dicarboximido) uroniumtetrafluoroborat (TNTU) or N, N, N, N-Tetramethyl-O-(N-succinimidyl) uroniumtetrafluorborat (TSTU).

14. The process of claim 6, wherein an optionally amino group protected amino $C_{4-8}$-alkyl linker is selected.

15. The process of claim 1, wherein the oligonucleotide consists of optionally modified DNA, RNA or LNA nucleoside monomers or combinations thereof and is 10 to 25 nucleotides in length.

16. The process of claim 10 wherein the polar aprotic solvent is N,N-dimethlylformamide.

* * * * *